(12) United States Patent
Imaizumi et al.

(10) Patent No.: US 7,636,414 B2
(45) Date of Patent: Dec. 22, 2009

(54) X-RAY CT APPARATUS AND IMAGE SELECTION METHOD THEREOF

(75) Inventors: Hideki Imaizumi, Kashiwa (JP); Masato Nakayama, Abiko (JP)

(73) Assignee: Hitachi Medical Corporation, Tokyo (JP)

( * ) Notice: Subject to any disclaimer, the term of this patent is extended or adjusted under 35 U.S.C. 154(b) by 218 days.

(21) Appl. No.: 10/544,564

(22) PCT Filed: Feb. 12, 2004

(86) PCT No.: PCT/JP2004/001469

§ 371 (c)(1),
(2), (4) Date: Aug. 5, 2005

(87) PCT Pub. No.: WO2004/071300

PCT Pub. Date: Aug. 26, 2004

(65) Prior Publication Data

US 2006/0140334 A1  Jun. 29, 2006

(30) Foreign Application Priority Data

Feb. 14, 2003   (JP) .............................. 2003-036309

(51) Int. Cl.
*A61B 6/00* (2006.01)
(52) U.S. Cl. ......................................................... 378/4
(58) Field of Classification Search ............... 378/4–20, 378/62, 901; 382/128, 131
See application file for complete search history.

(56) References Cited

U.S. PATENT DOCUMENTS

| | | | | |
|---|---|---|---|---|
| 4,458,267 A | * | 7/1984 | Dolazza ...................... | 378/98.7 |
| 5,841,890 A | * | 11/1998 | Kraske ........................ | 382/131 |
| 6,289,115 B1 | * | 9/2001 | Takeo ........................... | 382/130 |
| 6,501,822 B2 | * | 12/2002 | Roder .......................... | 378/22 |
| 6,574,304 B1 | * | 6/2003 | Hsieh et al. .................... | 378/62 |

(Continued)

FOREIGN PATENT DOCUMENTS

JP    9-107462    4/1997

(Continued)

OTHER PUBLICATIONS

International Preliminary Report on Patentability dated Feb. 23, 2006 in connection with PCT/JP2004/001469.

*Primary Examiner*—Edward J Glick
*Assistant Examiner*—Alexander H Taningco
(74) *Attorney, Agent, or Firm*—Cooper & Dunham, LLP (57) ABSTRACT

An X-ray CT apparatus comprises an X-ray generation device which generates X-rays, an X-ray detector which detects the X-rays having passed through a subject and outputs projection data, an imaging control device which controls the X-ray generation device and the X-ray detector so as to collect projection data, an image reconstruction device which reconstructs image data from the projection data, an image display device which displays an image on the basis of the image data, an image selection information addition device which adds, to the image data, the image selection information for the image data, an image selection device which judges presence/absence of an image analysis process on the basis of the image selection information and selects the image data, and an image analysis processing device which performs the image analysis process on the basis of the image data-selected by the image selection device.

20 Claims, 11 Drawing Sheets

U.S. PATENT DOCUMENTS

| | | | |
|---|---|---|---|
| 6,665,370 B2 * | 12/2003 | Bruder et al. | 378/15 |
| 6,765,983 B2 * | 7/2004 | Yan et al. | 378/8 |
| 6,999,549 B2 * | 2/2006 | Sabol et al. | 378/5 |

FOREIGN PATENT DOCUMENTS

| | | | |
|---|---|---|---|
| JP | 09-107462 | * | 4/1997 |
| JP | 9-223155 | | 8/1997 |
| JP | 10-143627 | | 5/1998 |
| JP | 63-313280 | | 12/1998 |
| JP | 2002-360559 | | 12/2002 |

* cited by examiner

X-RAY CT APPARATUS AND IMAGE SELECTION METHOD THEREOF

TECHNICAL FIELD

The present invention relates to an X-ray CT apparatus and an image selection method thereof and, more particularly, to an X-ray CT apparatus and an image selection method thereof which facilitate selection of a plurality of images targeted for image analysis processing out of a large amount of image data at the launch of an image analysis processing application.

BACKGROUND ART

An X-ray CT apparatus is an apparatus which creates a cross-sectional image of a subject using X-rays. In one collection data, the width in the direction of the body axis of a round slice (image slice thickness) is as small as about 1 cm. Accordingly, in one normal imaging operation, data of a plurality of parts are collected while moving a subject in the body axis direction, and a plurality of images are created within a certain range. Depending on circumstances, the range is imaged a plurality of number of times while reciprocating the subject. A multi-slice X-ray CT apparatus comprises a plurality of rows of X-ray detectors in the body axis direction and can collect data of a plurality of parts at a time. A combination of detectors makes it possible to create a plurality of images with different image slice thicknesses by one data collection operation.

A conventional apparatus needs to perform a plurality of imaging operations in order to obtain images with a plurality of image slice thicknesses. In contrast with this, a multi-slice CT allows creation of images with a plurality of image slice thicknesses at a time and shortens the time required for one test. This makes it possible to increase the range of data collection in one test operation and increase the number of tests to be performed within a predetermined time, thus increasing the number of images to be stored in an image storage region.

When selecting a desired one from images stored in the image storage region to perform image analysis processing using a plurality of created images, pieces of image accompanying information which serve as pieces of character information accompanying the pieces of image data and reduced images created from the pieces of image data are displayed in a list. The operator manually selects an image from the list (see Japanese Patent Laid-Open No. 9-223155).

However, in the case of images with different image slice thicknesses obtained by one imaging operation, they are substantially equal in parameters other than image slice thickness, and thus, it is difficult to select a desired image from a list of pieces of image accompanying information. If a change in imaging position on the same subject is about 1 mm, it is more difficult to distinguish among reduced images with different imaging positions than among normal-sized images. As described above, since the number of images to be created tends to increase in a multi-slice CT, list display of all images and selection operation become complicated. An object of the present invention is to facilitate such complicated image selection.

BRIEF SUMMARY

In an aspect of the present disclosure an X-ray CT apparatus is provided comprising an X-ray generation device which generates X-rays, an X-ray detector which detects the X-rays having passed through a subject and outputs projection data, an imaging control device which controls the X-ray generation device and the X-ray detector so as to collect the projection data, an image reconstruction device which reconstructs image data from the projection data, an image display device which displays an image on the basis of the image data, an image selection information addition device which adds, to the image data, image selection information for the image data, an image selection device which judges presence/absence of an image analysis process on the basis of the image selection information and selects the image data, and an image analysis processing device which performs the image analysis process on the basis of the image data selected by the image selection device.

In another aspect of the present invention, an image selection method for an X-ray CT apparatus is provided comprising a step of generating X-rays, a step of outputting projection data by detecting the X-rays having passed through a subject, a step of collecting the projection data by controlling the step of generating the X-rays and the step of outputting the projection data, a step of reconstructing image data from the projection data, a step of displaying an image on the basis of the image data, a step of adding, to the image data, image selection information for the image data, a step of judging presence/absence of an image analysis process on the basis of the image selection information and selecting the image data, and a step of performing the image analysis process on the basis of the selected image data.

BEST MODE FOR CARRYING OUT THE INVENTION

An embodiment of the present invention will be explained below in detail on the basis of the accompanying drawings.

Figure 1:
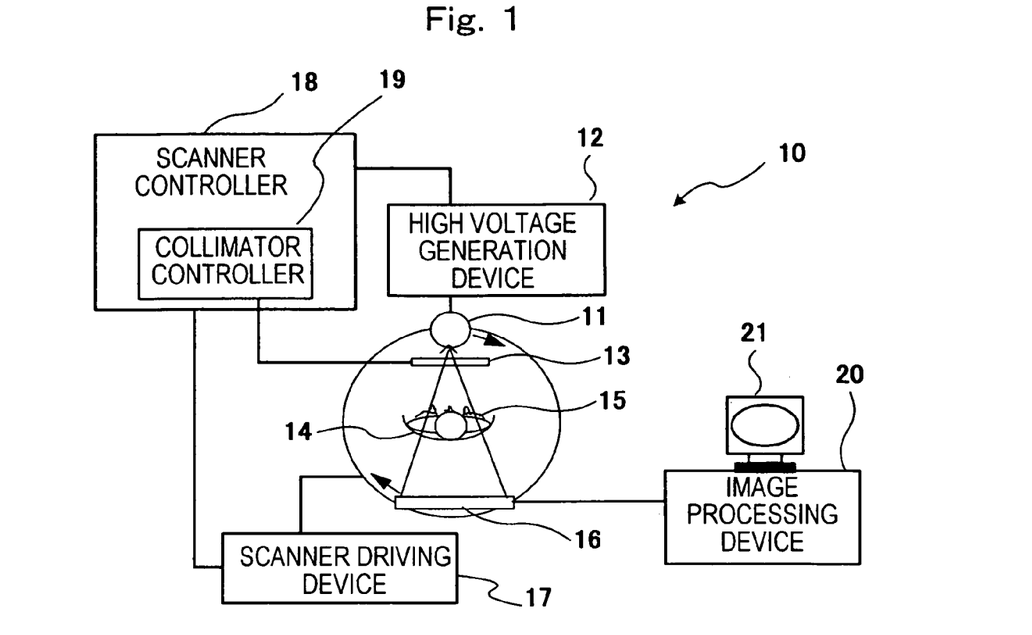
FIG. 1 is a view of the schematic arrangement of an X-ray CT apparatus according to an embodiment of the present invention.

FIG. 1 is a view of the schematic arrangement of an X-ray CT apparatus according to an embodiment of the present invention. An X-ray CT apparatus 10 mainly has an X-ray generation device 11 which generates X-rays, a high voltage generation device 12 which supplies a high voltage to the X-ray generation device 11, a collimator 13 which collimates X-rays generated by the X-ray generation device 11, a subject table 14 on which a subject 15 is to be mounted, a multi-row X-ray detector 16 which detects X-rays having passed through the subject 15, a scanner driving device 17 which causes a scanner main body having the X-ray generation device 11 and multi-row X-ray detector 16 to continuously rotate about its circumferential axis and at the same time causes the scanner main body and subject table 14 to continuously move relatively in the axial direction of the circumferential axis, a scanner controller 18 with which conditions for controlling the scanner can be input and which controls the scanner, a collimator controller 19 which controls the collimator 13, an image processing device 20 which performs pre-processing/image reconstruction processing and various types of analysis processes on the basis of projection data obtained from the multi-row X-ray detector 16, and a monitor 21.

X-rays in the shape of a cone or pyramid having a three-dimensional expanse are irradiated from the X-ray generation device 11 to a ROI (Region Of Interest) of the subject 15 on the subject table 14 through the collimator 13. The X-rays having passed through the subject 15 are detected by the multi-row X-ray detector 16 and are output as projection data to the image processing device 20. The image processing device 20 reconstructs a tomographic image from the input projection data and displays it on the monitor 21.

Figure 2:
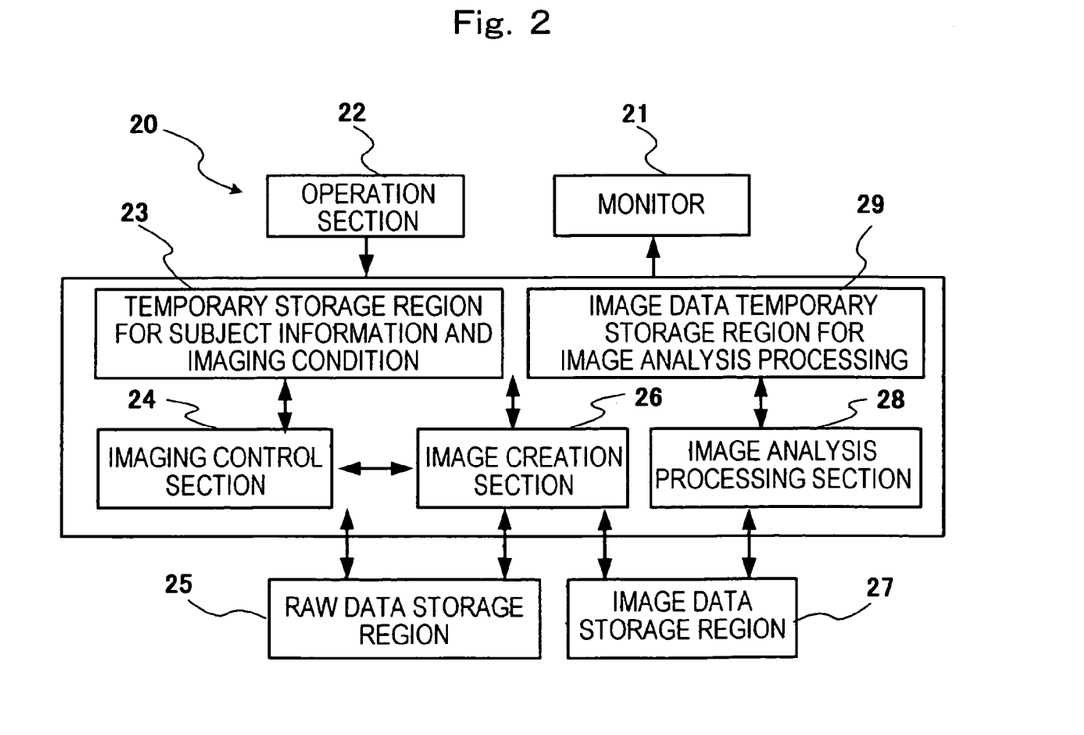
FIG. 2 is a block diagram showing the arrangement of an image processing device.

FIG. 2 is a block diagram showing the arrangement of the image processing device 20. The image processing device 20 mainly has an operation section 22 composed of a keyboard and a mouse, a temporary storage region 23 for subject information and imaging condition which temporarily stores subject information and imaging conditions, an imaging control section 24 which controls CT imaging and collects projection data, a raw data storage region 25 which stores raw data collected by the imaging control section 24, an image creation section 26 which reconstructs a CT image from projection data, an image data storage region 27 which stores image data created by the image creation section 26, an image analysis processing section 28 which performs image analysis processing on the basis of an image stored in the image data storage region 27, and an image data temporary storage region 29 for image analysis processing which temporarily stores image data required by the image analysis processing section 28.

Figure 3:
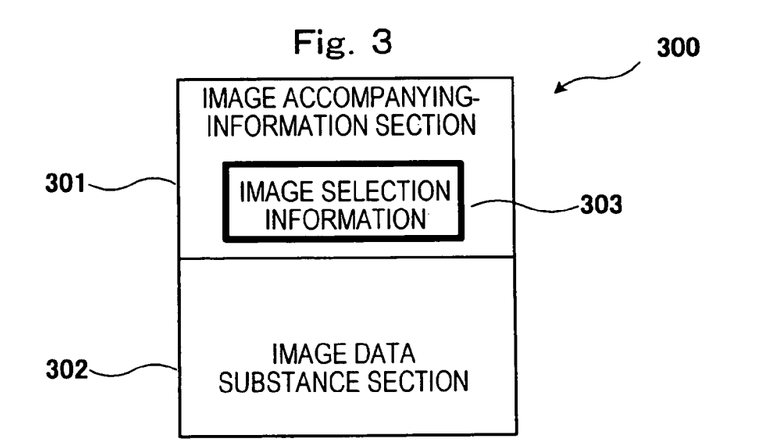
FIG. 3 is a diagram of the structure of image data.
Figure 4:
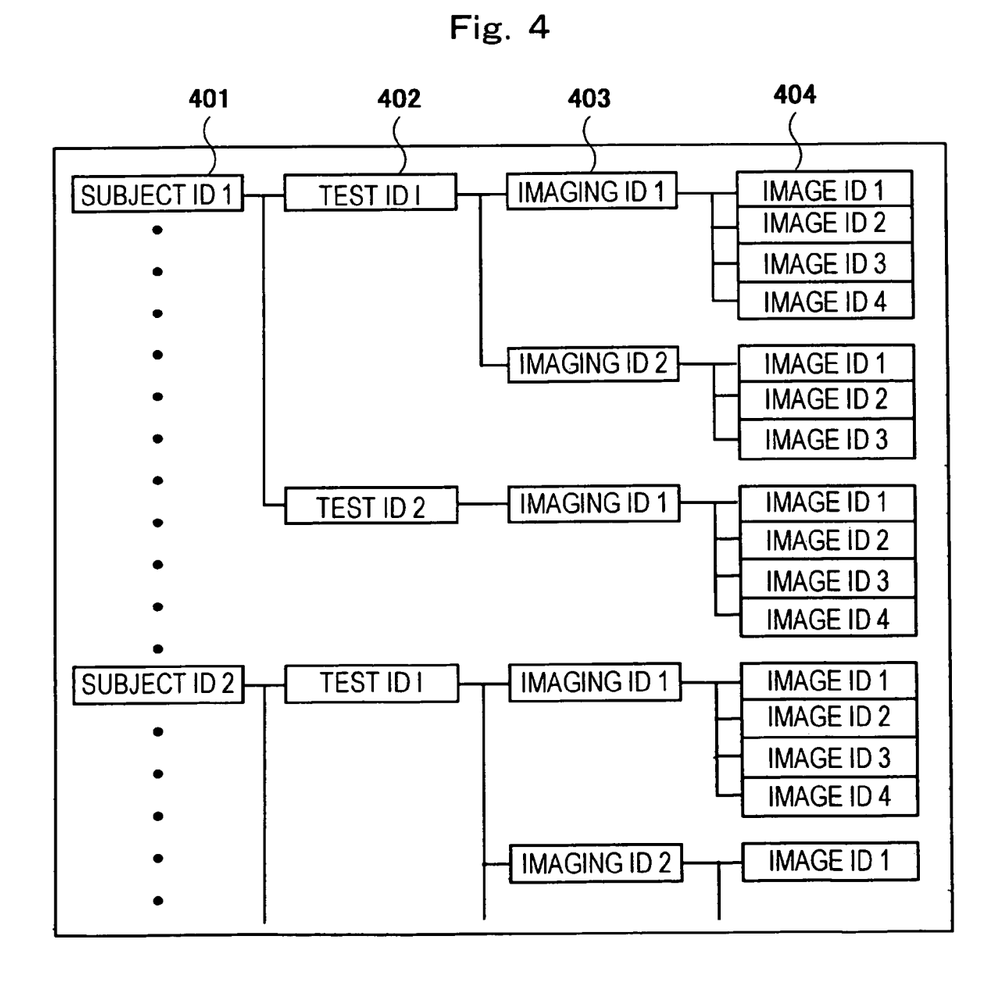
FIG. 4 is an image list in which a plurality of images are classified into a hierarchical structure.

Each of pieces 300 of image data stored in the image data storage region 27 is composed of an image accompanying-information section 301 and an image data substance section 302, as shown in FIG. 3. The pieces 300 of image data are distinguished by the parameters in their image accompanying-information sections 301. FIG. 4 shows an image list in which a plurality of images are classified into a hierarchical structure using the parameters in their image accompanying-information sections 301. The parameters in each image accompanying-information section 301 include a subject ID 401 which is a number assigned to each subject so as to be unique in the device, a test ID 402 which is assigned to each step, i.e., from beginning to end of one test on the basis of the test contents, test date, and the like, an imaging ID 403 which is assigned to each set of predetermined imaging conditions in one test, an image ID 404 which is a number assigned to each image, and a piece 303 of image selection information (to be described later).

Figure 5:
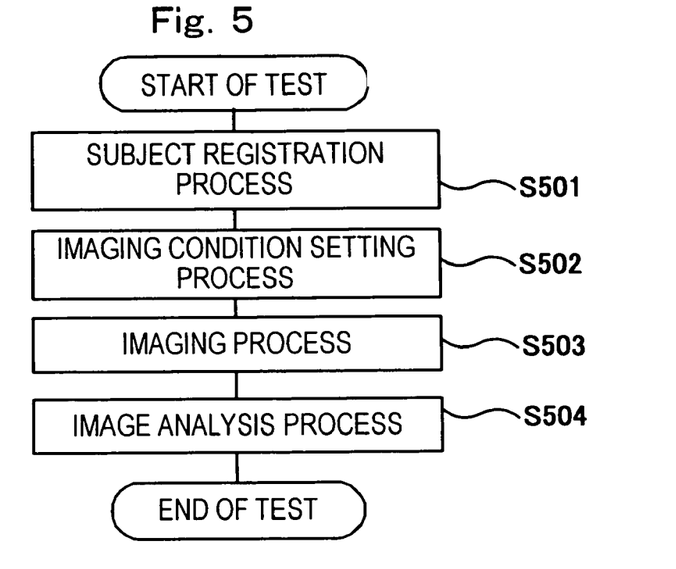
FIG. 5 is a flowchart showing the outline of one CT test.

FIG. 5 is a flowchart showing the outline of one CT test. First, in a subject registration process (S501), when the operator inputs, through the operation section 22, subject information (subject name, subject ID 401, test ID 402, and the like) while viewing the monitor 21, the input subject information is stored in the temporary storage region 23 for subject information and imaging condition. Then, in an imaging condition setting process (S502), when the operator inputs, through the operation section 22, various types of necessary imaging conditions (image slice thickness, tube current, and the like) and pieces of image selection information while viewing the monitor 21, the input imaging conditions and pieces of image selection information are set in the temporary storage region 23 for subject information and imaging condition. Since the imaging condition setting process is a condition setting process for one test ID, imaging conditions are set for each of a plurality of imaging IDs, as shown in FIG. 4. In an imaging process (S503), the imaging control section 24 performs data collection on the basis of the imaging conditions set in the temporary storage region 23 for subject information and imaging condition. The image creation section 26 performs image reconstruction on the basis of the projection data collected by the imaging control section 24 to create an image data substance section 302 and at the same time creates a corresponding image accompanying-information section 301 on the basis of the information stored in the temporary storage region 23 for subject information and imaging condition. The imaging control section 24 combines the image accompanying-information section 301 with the image data substance section 302 to create a piece 300 of image data and stores the created piece 300 of image data into the image data storage region 27. Last, in an image analysis process (S504), the image analysis processing section 28 writes necessary pieces of image data from the image data storage region 27 into the image data temporary storage region 29 for image analysis processing while referring to the pieces of image selection information and performs various types of image analysis processes using the pieces of image data. This operation by the image analysis processing section 28 of writing necessary images from the image data storage region 27 into the image data temporary storage region 29 for image analysis processing will be referred to as image selection.

Image analysis processes here refer to a three-dimensional reconstruction process, image addition/subtraction process, edge enhancement process, smoothing process, CT value conversion process, maximum intensity projection image process, arbitrary cross-sectional image display process, and three-dimensional image display process. Since image selection is also performed in a film print process, cinedisplay (automatic, continuous image display) process, image transfer process (including DICOM (Digital Imaging and Communications in Medicine) transfer) through a network, and the like, these processes will be also included in the image analysis processes.

Each piece 303 of image selection information that is set in the imaging condition setting process (S502) and is included in a corresponding image accompanying-information section 301 is information for specifying in advance whether to target a created image for the image analysis processes and for specifying in advance which image analysis process the created image is to be targeted if the image is targeted. In conventional technique, the operator needs to manually select an image on the basis of pieces of ID information such as subject IDs 401, test IDs 402, imaging IDs 403, image IDs 404, and the like contained in the image accompanying-information section 301 when performing image analysis processing. In contrast with this, according to this embodiment, special preparation of pieces 303 of image selection information which specify in advance analysis processes for the corresponding pieces 300 of image data as parameters in the image accompanying-information sections 301 makes it possible to automatically select an image when performing image analysis processing.

Figure 6:
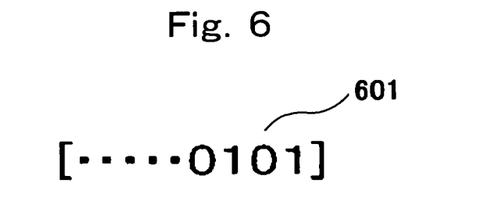
FIG. 6 is a view of the data structure of a piece of image selection information.

FIGS. 6 to 8 show embodiments of the data structure of each piece 303 of image selection information. In the embodiment of FIG. 6, the piece 303 of image selection information is denoted by flags 601 indicating the ON/OFF states for respective image analysis processes. The types of image analysis processes are associated in advance with the positions of the flags in data. Depending on whether to set each piece 300 of image data as the target for a certain image analysis process, a flag at a position corresponding to the image analysis process is set to "1" or "0." This allows bitwise handling of each piece 303 of image selection information and thus avoids compression of the size of the storage region of the corresponding image accompanying-information section 301.

Figure 7:
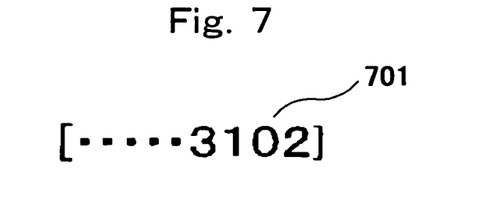
FIG. 7 is a view of the data structure of another piece of image selection information.

In the embodiment of FIG. 7, each piece 303 of image selection information is denoted by integral values 701 indicating the order of image analysis processes. As in the embodiment of FIG. 6, the types of image analysis processes are associated in advance with the positions of flags in data. The example shown in FIG. 7 denotes that when performing image analysis processing, an image analysis process corresponding to the position of a flag "3" is performed in the third place, an image analysis process corresponding to the position of a flag "1" is performed in the first place, an image analysis process corresponding to the position of a flag "0" is not performed, and an image analysis process corresponding to the position of a flag "2" is performed in the second place. This makes it possible to automatically perform a plurality of image analysis processes in a desired order.

Figure 8:
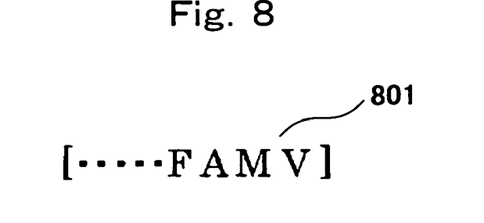
FIG. 8 is a view of the data structure of still another piece of image selection information.

In the embodiment of FIG. 8, each piece 303 of image selection information is denoted by characters 801 indicating the contents of image analysis processes to be performed. The types of image analysis processes are associated in advance with the characters. The term "characters" here include numeric characters and symbols. The example shown in FIG. 8 denotes that when performing image analysis processing, an image analysis process corresponding to a character "F", an image analysis process corresponding to a character "A", an image analysis process corresponding to a character "M", and an image analysis process corresponding to a character "V" are performed in this order. This makes it possible to automatically perform a plurality of image analysis processes in a desired order. In addition, it is unnecessary to associate in advance the types of image analysis processes with the positions of flags in data, unlike the embodiments explained in FIGS. 6 and 7. Advantageously, this embodiment need not decide in advance the position of each piece 303 of image selection information in parameters.

Figure 9:
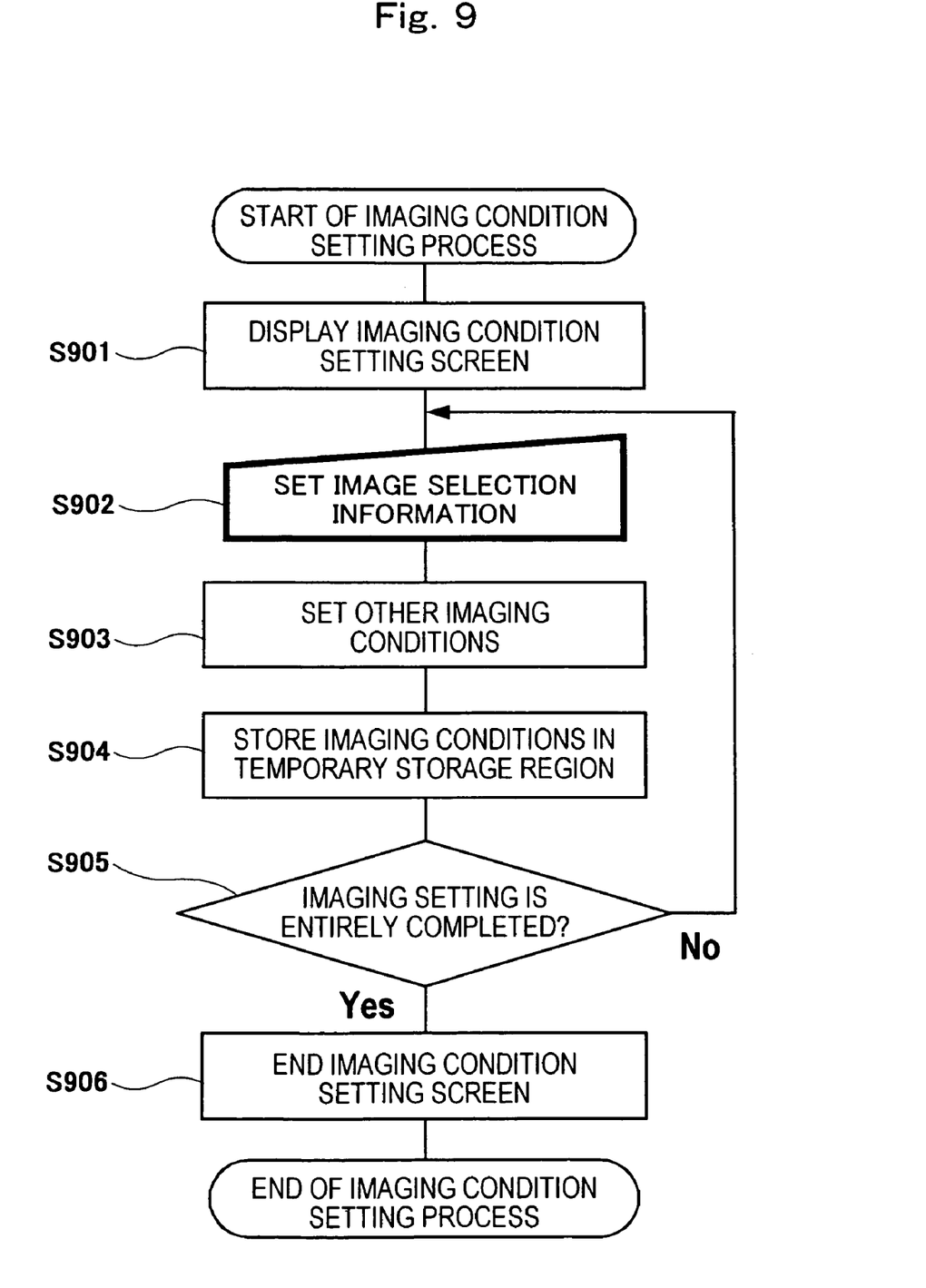
FIG. 9 is a flowchart showing the details of an imaging condition setting process.

FIG. 9 is a flowchart showing the details of the imaging condition setting process (S502) of FIG. 5. First, an imaging condition setting screen is displayed on the monitor 21 (S901). A piece of image selection information is displayed as an imaging condition on the imaging condition setting screen to make the operator input the piece of image selection information through the operation section 22 (S902). The operator is made to input other imaging conditions as well (S903), and the input piece of image selection information and other imaging conditions are stored in the temporary storage region 23 for subject information and imaging condition (S904). When the condition setting is completed for the imaging IDs of a test (S905), the imaging condition setting screen ends (S906).

Figure 10:
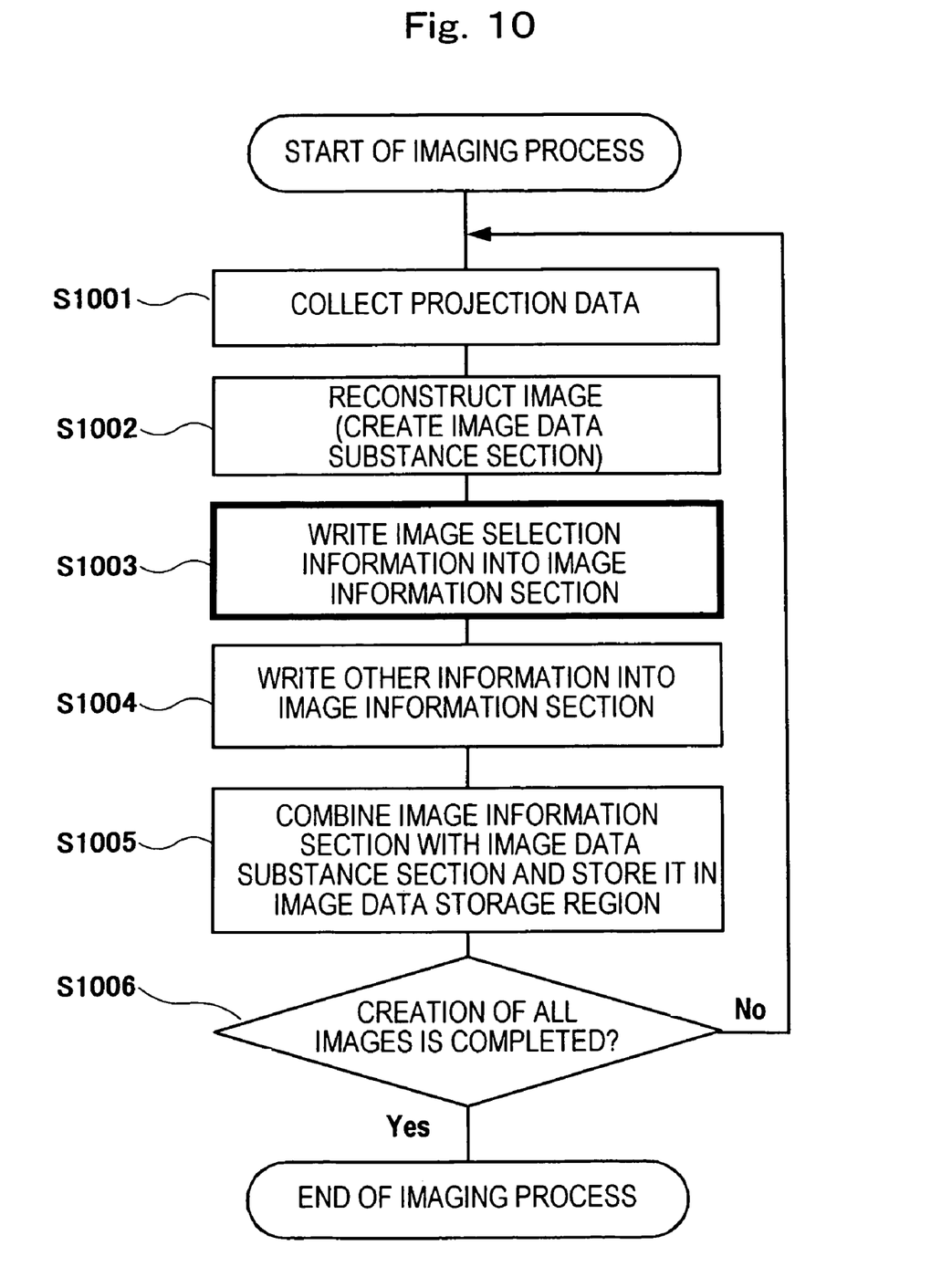
FIG. 10 is a flowchart showing the details of an imaging process.

FIG. 10 is a flowchart showing the details of the imaging process (S503) of FIG. 5. First, projection data is collected (S1001), and an image data substance section 302 is created by an image reconstruction process (S1002). A piece of image selection information stored in the temporary storage region 23 for subject information and imaging condition is written into the piece 303 of image selection information of a corresponding image accompanying-information section 301 (S1003), and other necessary information stored in the temporary storage region 23 for subject information and imaging condition is written into the image accompanying-information section 301 (S1004). The image accompanying-information section 301 is combined with the image data substance section 302 to create a piece 300 of image data, and the created piece 300 of image data is stored into the image data storage region 27 (S1005). When the imaging processing is completed for all images (S1006), the imaging process ends.

Figure 11:
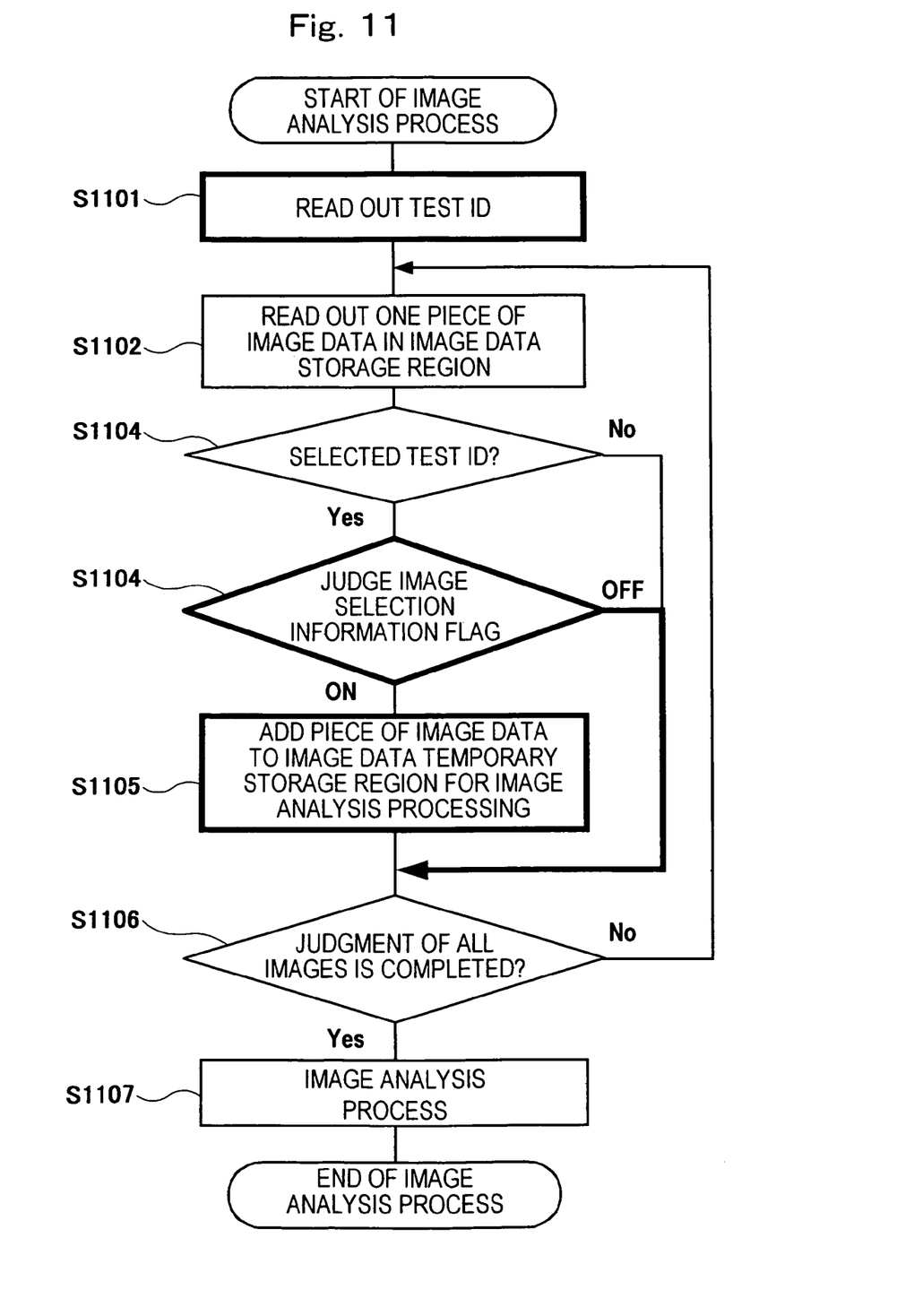
FIG. 11 is a flowchart showing the details of an image analysis process.

FIG. 11 is a flowchart showing the details of the image analysis process (S504) of FIG. 5. First, a subject ID 401 and test ID 402 stored in the temporary storage region 23 for subject information and imaging condition in the subject registration process (S501) are read out (S1101). Then, a piece 300 of image data for one image is read out from the pieces 300 of image data in the image data storage region 27 (S1102). The test IDs 402 read out from the temporary storage region 23 for subject information and imaging condition is compared with the test ED 402 in the image accompanying-information section 301 of the piece 300 of image data read out from the image data storage region 27 (S1103). If the test IDs are equal, it is judged whether the piece 303 of image selection information in the image accompanying-information section 301 of the read-out piece 300 of image data has specified in S502 that a called image analysis process is to be performed (S1104). If the piece 303 of image selection information has specified that, the piece 300 of image data is additionally stored in the image data temporary storage region 29 for image analysis processing (S1105). When the judgment processing is completed for all pieces of image data in the image data storage region 27 (S1106), an image analysis process is performed using pieces of image data in the image data temporary storage region 29 for image analysis processing (S1107). For this reason, only the operation by the operator of launching an image analysis process application allows completely automatic image selection, and the device operability is improved.

Figure 12:
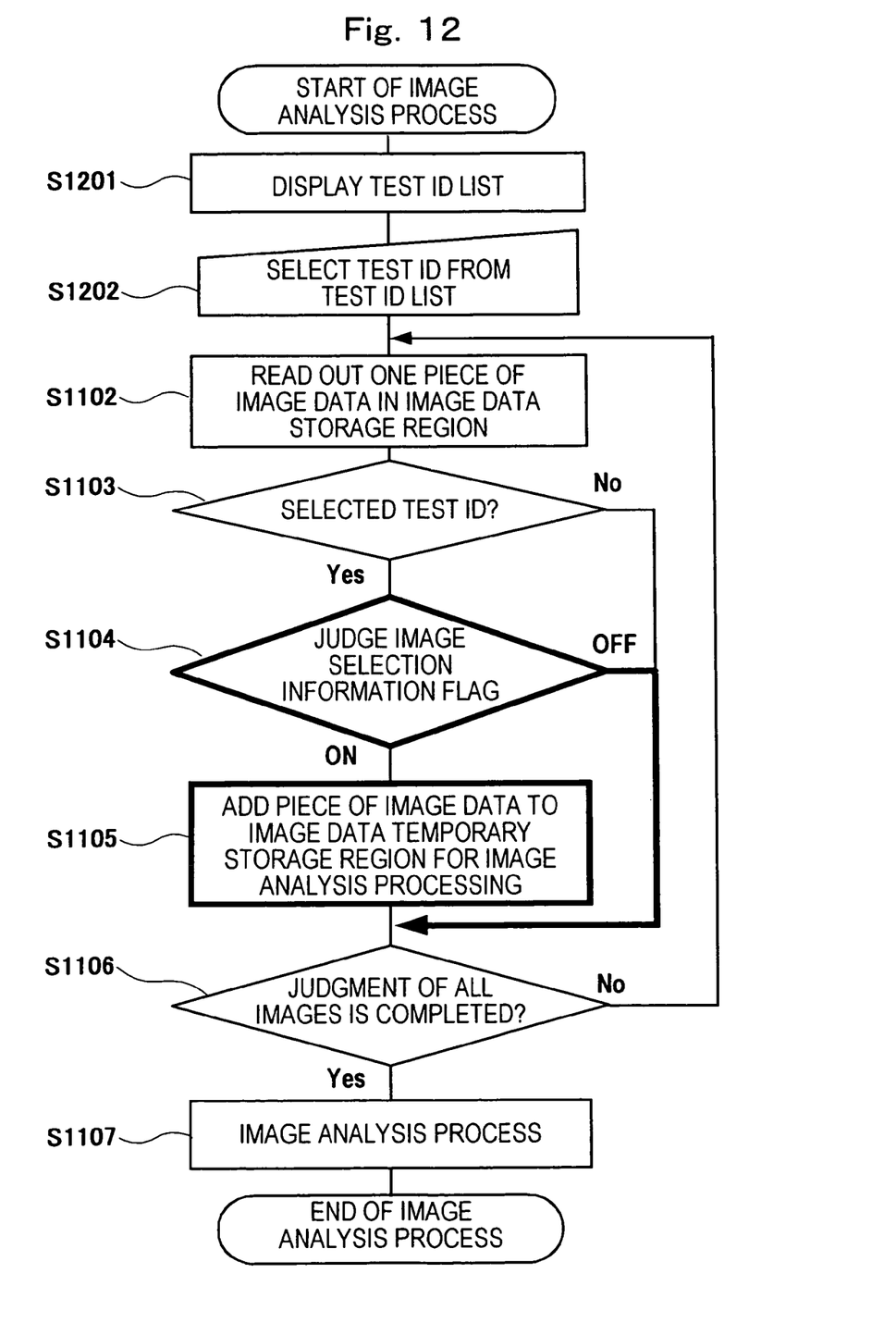
FIG. 12 is a flowchart showing a modification of the image analysis process.

FIG. 12 is a flowchart showing a modification of the image analysis process (S504) of FIG. 5. First, a subject ID 401 stored in the temporary storage region 23 for subject information and imaging condition in the subject registration process (S501) is read out. The test IDs 402 in images where subject IDs 401 equal to the read-out subject ID 401 are set are read out from all pieces of image data in the image data storage region 27 and are displayed in a list (S1201). The operator is made to select a desired one of the test IDs 402 from the test ID list (S1202). Processes in S1102 and subsequent steps are the same as those explained in FIG. 11. Since if one wants to compare images with those in the previous test, or the like, selection of images of the same subject with different test IDs 402 is necessary, a test ID list is useful. In the embodiment of FIG. 12, only the operation by the operator of selecting a test ID from a list allows automatic image selection, and the device operability is improved.

Figure 13:
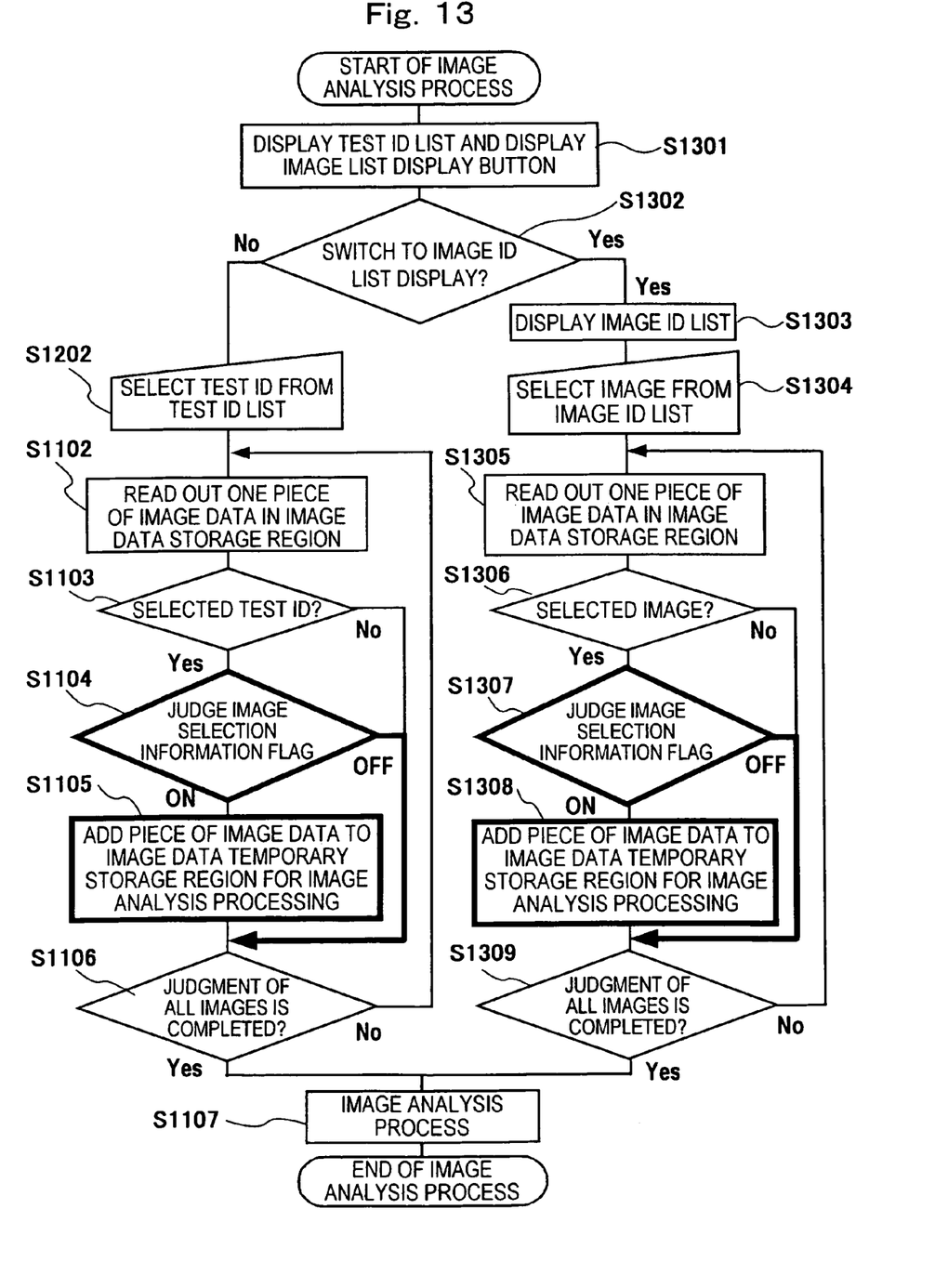
FIG. 13 is a flowchart showing another modification of the image analysis process.

FIG. 13 is a flowchart showing another modification of the image analysis process (S504) of FIG. 5. First, a subject ID 401 stored in the temporary storage region 23 for subject information and imaging condition in the subject registration process (S501) is read out. The test IDs 402 in images where subject IDs 401 equal to the read-out subject ID 401 are set are read out from all pieces of image data in the image data storage region 27 and are displayed in a list on the monitor 21. An image ID list display button for switching from test ID list display to list display of all pieces of image data in the image data storage region 27 is also displayed on the list display screen (S1301). The operator is made to choose (S1302) either, the selection from test IDs 402 on the display list, or to switch to the image ID list. If the operator has not pressed the image ID list display button, he/she is made to select a desired one of the test IDs 402 from the test ID list (S1202). Processes in S1202 and subsequent steps are the same as those explained in FIG. 12. On the other hand, if the operator has pressed the image ID list display button in S1302, display is switched from the test ID list to the image ID list of all pieces of image data in the image data storage region 27 (S1303). The operator is made to select a desired one of image IDs 404 from the image ID list (S1304). A piece 300 of image data for one image is read out from pieces 300 of image data in the image data storage region 27 (S1305), and the image ID 404 selected by the operator is compared with the image ID 304 in the image accompanying-information section 301 of the piece 300 of image data read out from the image data storage region 27 (S1306). If the image IDs are equal, it is judged whether the piece 303 of image selection information in the image accompanying-information section 301 of the read-out piece 300 of image data has specified in S502 that a called image analysis process is to be performed (S1307). If the piece 303 of image selection information has specified that, the piece 300 of image data is additionally stored in the image data temporary storage region 29 for image analysis processing (S1308). When the judgment processing is completed for all the pieces of image data in the image data storage region 27 (S1309), the image analysis process is performed using pieces of image data in the image data temporary storage region 29 for image analysis processing (S1107). This makes it possible for the operator to select one of automatic image selection and conventional manual image ID selection operation.

The above-described embodiment has explained an example wherein projection data collection, image reconstruction, and image analysis are performed in succession. The present invention, however, is not limited to this. The present invention can also be applied to postreconstruction in which raw projection data collected at the time of imaging is stored, and image reconstruction is performed later using the stored projection data.

Figure 14:
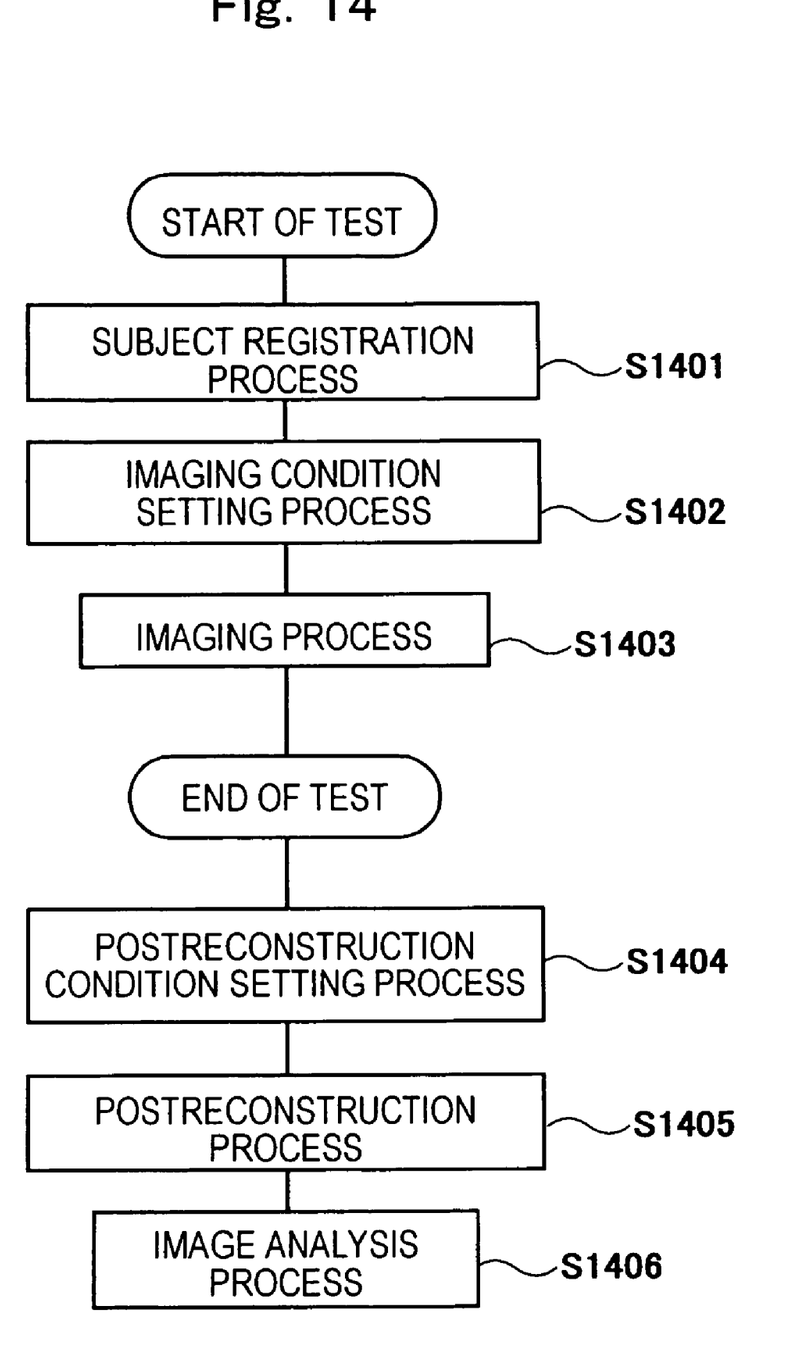
FIG. 14 is a flowchart showing the outline of a process when postreconstruction is performed.

FIG. 14 is a flowchart showing the outline of a process when postreconstruction is performed. First, in a subject registration process (S1401), the operator inputs, through the operation section 22, subject information (subject name, subject ID 401, test ID 402, and the like) while viewing the monitor 21, the input subject information is stored in the temporary storage region 23 for subject information and imaging condition. Then, in an imaging condition setting process (S1402), when the operator inputs, through the operation section 22, various types of necessary imaging conditions (image slice thickness, tube current, and the like) while viewing the monitor 21, the input imaging conditions are set in the temporary storage region 23 for subject information and imaging condition. In an imaging process (S1403), the imaging control section 24 performs data collection on the basis of the imaging conditions set in the temporary storage region 23 for subject information and imaging condition, and the projection data collected by the imaging control section 24 is stored in the raw data storage region 25. The test ends as a temporary measure, and a postreconstruction process starts at an arbitrary time. First, in a postreconstruction condition setting process (S1404), when the operator inputs, through the operation section 22, various types of necessary postreconstruction conditions (image slice thickness and the like) and pieces of image selection information while viewing the monitor 21, the input postreconstruction conditions and pieces of image selection information are set in the temporary storage region 23 for subject information and imaging condition. In a postreconstruction process (S1405), the image creation section 26 performs image reconstruction on the basis of the projection data stored in the raw data storage region 25 to create an image data substance section 302 and at the same time creates a corresponding image accompanying-information section 301 on the basis of the information stored in the temporary storage region 23 for subject information and imaging condition. The imaging control section 24 combines the image accompanying-information section 301 with the image data substance section 302 to create a piece 300 of image data and stores the created piece 300 of image data into the image data storage region 27. Last, in an image analysis process (S1406), the image analysis processing section 28 writes necessary pieces of image data from the image data storage region 27 into the image data temporary storage region 29 for image analysis processing while referring to the pieces of image selection information and performs various types of image analysis processes using the pieces of image data.

Figure 15:
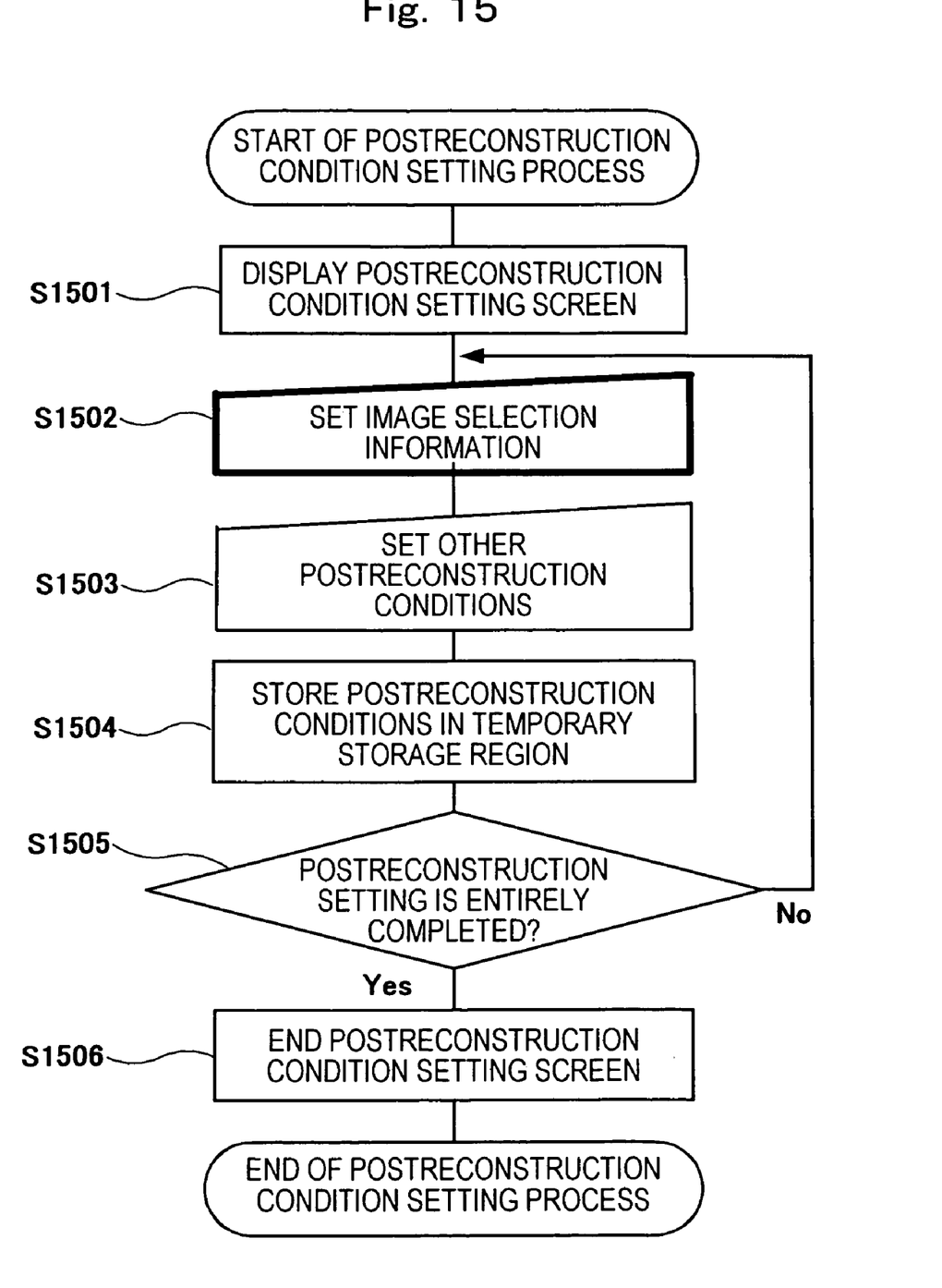
FIG. 15 is a flowchart showing the details of a postreconstruction condition setting process.

FIG. 15 is a flowchart showing the details of the postreconstruction condition setting process (S1404) of FIG. 14. First, a postreconstruction condition setting screen is displayed on the monitor 21 (S1501). A piece of image selection information is displayed as a postreconstruction condition on the postreconstruction condition setting screen to make the operator input the piece of image selection information through the operation section 22 (S1502). The operator is made to input other postreconstruction conditions as well (S1503), and the input piece of image selection information and other postreconstruction conditions are stored in the temporary storage region 23 for subject information and imaging condition (S1504). When the setting of necessary postreconstruction conditions is completed (S1505), the postreconstruction condition setting screen ends (S1506).

Figure 16:
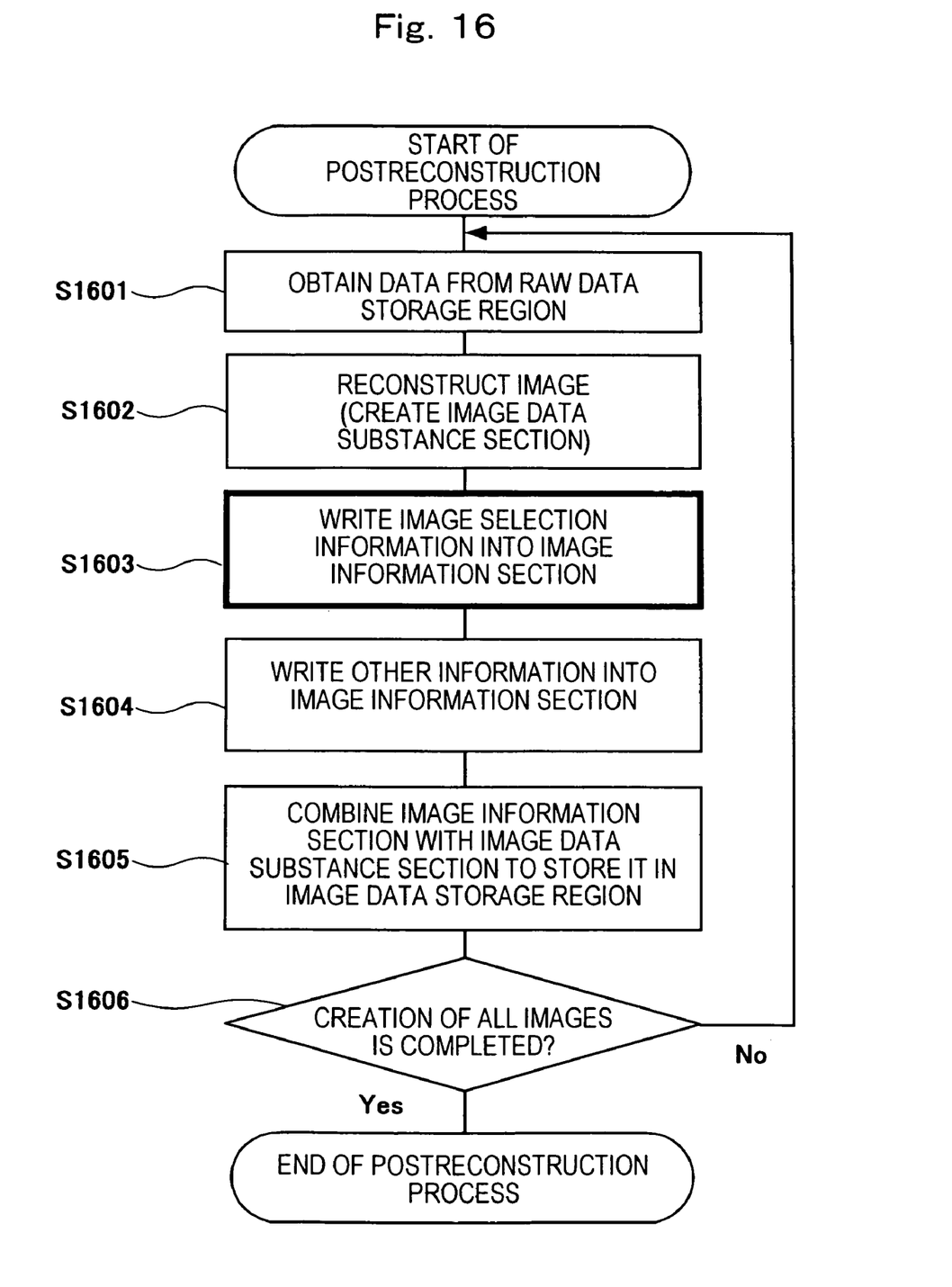
FIG. 16 is a flowchart showing the details of a postreconstruction process.

FIG. 16 is a flowchart showing the details of the postreconstruction process (S1405) of FIG. 14. First, stored raw projection data is obtained from the raw data storage region 25 (S1601), and an image data substance section 302 is created by an image reconstruction process (S1602). A piece of image selection information stored in the temporary storage region 23 for subject information and imaging condition is written into the piece 303 of image selection information of a corresponding image accompanying-information section 301 (S1603), and other necessary information stored in the temporary storage region 23 for subject information and imaging condition is written into the image accompanying-information section 301 (S1604). The image accompanying-information section 301 is combined with the image data substance section 302 to create a piece 300 of image data, and the created piece 300 of image data is stored into the image data storage region 27 (S1605). When the postreconstruction processing is completed for all images (S1606), the postreconstruction process ends.

The image analysis process (S1406) of FIG. 14 is the same as those (S1107) explained in FIGS. 11, 12, and 13.

INDUSTRIAL APPLICABILITY

As has been explained above, according to the present invention, the operation of selecting an image targeted for image analysis processing is facilitated, and the device operability is improved.

The invention claimed is:

1. An X-ray CT apparatus, comprising:
an X-ray generation device which generates X-rays;
an X-ray detector which detects the X-rays having passed through a subject and outputs projection data;
an imaging control device which controls the X-ray generation device and the X-ray detector so as to collect the projection data;
an image reconstruction device which reconstructs a plurality of pieces of image data using a plurality of pieces of the projection data;
an image display device which displays an image on the basis of the image data;
an image selection information addition device which adds image selection information to each piece of image data as accompanying information of the piece of image data, the image selection information being information for specifying in advance whether the piece of image data is targeted for an image analysis process, at least;
an image selection device which judges whether each piece of image data is targeted or not for the image analysis process on the basis of the image selection information by subject information and selects one or more pieces of image data which are judged to be targeted for the image analysis process from among the plurality of pieces of image data; and
an image analysis processing device which performs the image analysis process on the basis of the one or more selected pieces of image data selected by the image selection device.

2. The X-ray CT apparatus according to claim 1, wherein the X-ray detector comprises a plurality of rows of X-ray detectors in a direction of a body axis of the subject.

3. The X-ray CT apparatus according to claim 1, wherein the image selection information is a flag indicating an ON/OFF state of each image analysis process.

4. The X-ray CT apparatus according to claim 3, wherein:
a type of each image analysis process is associated in advance with a position of each flag; and
the image selection information addition device sets a flag at a position corresponding to a certain image analysis process to one or zero, depending on whether the piece of image data is targeted for the certain image analysis process.

5. The X-ray CT apparatus according to claim 1, wherein the image selection information is an integral value indicating an order of an image analysis process.

6. The X-ray CT apparatus according to claim 5, wherein:
a type of each image analysis process is associated in advance with a position of each flag; and
the image selection information addition device determines the integral value of a flag at a position corresponding to the image analysis process, depending on the order of the image analysis process.

7. The X-ray CT apparatus according to claim 1, wherein the image selection information is a character indicating contents of an image analysis process to be performed.

8. The X-ray CT apparatus according to claim 7, wherein:
a type of each image analysis process is associated in advance with a character; and
the image selection information addition device generates a flag in which characters are arranged, depending on an order of the image analysis process.

9. The X-ray CT apparatus according to claim 1, wherein the image selection information is set before collection of the projection data and is added to the image data after the image data is reconstructed from the projection data.

10. The X-ray CT apparatus according to claim 1, further comprising
a projection data storage device which stores the projection data, wherein the image reconstruction device reconstructs the image data from the projection data stored in the projection data storage device, and
the image selection information is set after collection of the projection data and is added to the image data after the image data is reconstructed from the projection data.

11. The X-ray CT apparatus according to claim 1, further comprising:
a storage region that stores pieces of image data to which the image selection information is added; and
a temporary storage region that stores a piece of image data required by an image analysis processing device, wherein the image selection device writes a piece of image data that is to be subjected to image analysis process among pieces of image data stored in the storage region into an image data temporary storage region.

12. The X-ray CT apparatus according to claim 1, wherein the image selection information indicates at least one of the following candidate processes to be selected for the image analysis process, if said image selection device judges that the image analysis process is necessary: three-dimensional reconstruction process; image addition/subtraction process; edge enhancement process; smoothing process; CT value conversion process; maximum intensity projection image process; and arbitrary cross-sectional image display process.

13. An image selection method for an X-ray CT apparatus, comprising:
a step of generating X-rays;
a step of outputting projection data by detecting the X-rays having passed through a subject;
a step of collecting the projection data by controlling the step of generating the X-rays and the step of outputting the projection data;
a step of reconstructing a plurality of pieces of image data using a plurality of pieces of the projection data;
a step of displaying an image on the basis of the image data;
a step of adding image selection information to each piece of image data as accompanying-information of the piece of image data, the image selection information being information for specifying in advance whether the piece of image data is targeted for an image analysis process, at least;
a step of judging whether each piece of image data is targeted or not for the image analysis process on the basis of the image selection information by subject information and selecting one or more pieces of image data which are judged to be targeted for the image analysis process from among the plurality of pieces of image data; and
a step of performing the image analysis process on the basis of the one or more selected pieces of image data.

14. The image selection method for the X-ray CT apparatus according to claim 13, wherein the step of outputting the projection data is performed by an X-ray detector comprising a plurality of rows of X-ray detectors in a direction of a body axis of the subject.

15. The image selection method for the X-ray CT apparatus according to claim 13, wherein the image selection information is a flag indicating an ON/OFF state of each image analysis process.

16. The image selection method for the X-ray CT apparatus according to claim 13, wherein the image selection information is an integral value indicating an order of an image analysis process.

17. The image selection method for the X-ray CT apparatus according to claim 13, wherein the image selection information is a character indicating contents of an image analysis process to be performed.

18. The image selection method for the X-ray CT apparatus according to claim 13, wherein the step of adding the image selection information comprises:
   a step of setting the image selection information before the step of collecting the projection data; and
   a step of adding the image selection information to the image data after the step of reconstructing the image data.

19. The image selection method for the X-ray CT apparatus according to claim 13, further comprising a step of storing the projection data,
   wherein in the step of reconstructing the image data, the image data is reconstructed from the projection data stored in the step of storing the projection data, and
   wherein the step of adding the image selection information comprises:
   a step of setting the image selection information after the step of storing the projection data; and
   a step of adding the image selection information to the image data after the step of reconstructing the image data.

20. The image selection method according to claim 13, wherein in the step of selecting image data, a piece of image data that is to be subjected to image analysis process among pieces of image data stored in a storage region is written into an image data temporary storage region.

* * * * *